United States Patent [19]
Venter et al.

[11] Patent Number: 5,418,160
[45] Date of Patent: May 23, 1995

[54] CLONED CELL LINE EXPRESSING RAT $\beta_{3A}$ ADRENERGIC RECEPTOR

[75] Inventors: J. Craig Venter; Claire M. Fraser, both of Silver Spring, Md.; Jean-Paul Giacobino, Geneva, Switzerland

[73] Assignee: The United States as represented by the Secretary of the Department of Health and Human Services, Washington, D.C.

[21] Appl. No.: 783,602

[22] Filed: Nov. 1, 1991

[51] Int. Cl.$^6$ .................................................. C12N 5/10
[52] U.S. Cl. ................................. 435/240.2; 530/350; 536/23.5
[58] Field of Search ...................... 530/350; 435/240.2, 435/6

[56] References Cited

U.S. PATENT DOCUMENTS

5,288,607  2/1994  Emorine et al. .......................... 435/6

FOREIGN PATENT DOCUMENTS

9008775  8/1990  WIPO .

OTHER PUBLICATIONS

Nahmias et al., *EMBO J.* 10(12), 3721–3727 (1991).
Muzzin et al., *J. Biol. Chem.* 266(35), 24053–24058 (1991).
Arch et al, *Nature* 309, 163–165.
Emorine et al., *Scinece* 245, 1118–1121.
Foster et al., "Nonshivering Thermogenesis in the Rat. II. Measurements of Blood Flow with Microspheres Point to Brown Adipose Tissue as the Dominant Site of the Calorigenesis Induced By Noradrenaline", Can. J. Physiol., vol. 56, 110 (1978).
Rothwell et al., "A Role for Brown Adipose Tissue in Diet–Induced Thermogenesis", Nature (London), vol. 281, 31 (1979).
C. A. Machida et al., "Molecular Cloning and Expression of the Rat $\beta_1$–Adrenergic Receptor Gene", J. Biol Chem 265, 12960 (1990).
D. A. Robinson, "Molecular Characterization of Cardiac $\beta$–Adrenergic Receptors", Thesis, State University of New York at Buffalo (1988).
F. Z. Chung et al., "Cloning and Sequence Analysis of the Human Brain $\beta$–Adrenergic Receptor", FEBS Lett. 211, 200 (1987).
R. A. F. Dixon et al., "Structural–Function Analysis of the $\beta$–Adrenergic Receptor", Cold Spring Harbor Symp. Quant. Biol. 53, 487 (1988).
J. C. Venter et al., "Commentary: Molecular Biology of Adrenergic and Muscarinic Cholinergic Receptors", Biochem. Pharmacol. 38,1197 (1980).
C. M. Fraser, "Site–Directed Mutagenesis of $\beta$–Adrenergic Receptors", J. Biol. Chem., 264, 9266 (1989).
C. F. Strader, et al. "Structural Basis of $\beta$–Adrenergic Receptor Function", FASEB J. 3, 1825 (1989).
F. Z. Chung, et al. "Communication: Site-Directed Mutagenesis and Continuous Expression of Human $\beta$–Adrenergic Receptors", J. Biol. Chem. 263, 4052 (1988).
H. Lehrach, et al. "RNA Molecular Weight Determinations by Gel Electrophorisis under Denaturing Conditons, A Critical Reexamination", Biochem. 16, 4743 (1977).

(List continued on next page.)

*Primary Examiner*—Margaret Parr
*Assistant Examiner*—Kenneth R. Horlick
*Attorney, Agent, or Firm*—Lowe, Price, LeBlanc & Becker

[57] ABSTRACT

The present invention relates to a fat cell specific rat $\beta$-adrenergic receptor that mediates lipolysis in rats. The invention further relates to cloned cells which code for the specific $\beta$-adrenergic receptor that mediates lipolysis. Another aspect of the present invention relates to a diagnostic test method for determining decreased levels of fat cell $\beta$-adrenergic receptors that mediate lipolysis in order to diagnosis obesity caused by less active lipolysis.

1 Claim, 9 Drawing Sheets

OTHER PUBLICATIONS

J. Gocayne et al., "Primary Structure of Rat Cardiac β-Adrenergic and Muscarinic Cholinergic Receptor Obtained by Automated DNA Sequence Analysis: Further Evidence for a Multigene Family", Proc. Natl. Acad. Sci. USA 84, 8296 (1987).

J. Himms-Hagen, "Brown Adipose Tissue Thermogenesis and Obesity", Prog. Lip. Res. 28, 67 (1989).

F. Assimacopoulos-Jeannet, et al. "Alterations of Brown Adipose Tissue in Genetically Obese (ob/ob) Mice. II. Studies of β-Adrenergic Receptors and Fatty Acid Degradaton", Endocrinol. 110, 439 (1982).

A. Marette, et al. "Defective Metabolic Effects of Norepinephrine and Insulin in Obese Zucker Rat Brown Adipose Tissue", Am. J. Physiol. 258, E320 (1990).

P. Muzzin, et al. "The Novel Thermogenic β-Adrenergic Agonsit Ro 16-8714 Increases the Interscapular Brown-Fat β-Receptor-Adenylate Cyclase and the Upcoupling-Protein mRNA Level in Obese (fa/fa) Zucker Rats", Biochem J. 261, 721 (1989).

| | | | | |
|---|---|---|---|---|
| Human β2 | 1 | | gqpGNgSaFLL | APNrShAPdHDvTQgRDEvWVVGMgIvMSLI |
| Rat β2 | 1 | | hGNdSdFLL | APNgSrAPgHDiTQeRDEaWVVGMaIlMSvI |
| Rat β1 | 1 | M | MGAGaLaLGASEPcNLSSAAPLPDGAATAARLLVlASPPASEgsaPLSQQWTAGMGLLlALI |
| Human β1 | 1 | MEP | MGAGvLvlGASEPgNLSSAAPLPDGAATAARLLVpASPPASEspePLSQQWTAGMGLLmALI |
| Human β3 | 1 | MAPWPHENSSLAPWPD | lPTLaPntANTSGLP | GVPWeAALAG ALL ALA |
| Rat β3 | 1 | MAPWPHkNgSLafwsD | aPTLdPsaANTSGLP | GVPWaAALAG ALL ALA |
| | | * | | ▬▬▬▬▬▬ |
| | | | | I |

| | | | |
|---|---|---|---|
| Human β2 | 44 | VLAIVFGNVLVITAIAKFERLQTVTNYFITSLACADLVMGLAVVPFGAaHILMKMWtFGNFWCEFWTS |
| Rat β2 | 44 | VLAIVFGNVLVITAIAKFERLQTVTNYFITSLACADLVMGLAVVPFGAsHILMKMWnFGNFWCEFWTS |
| Rat β1 | 69 | VLLIVGNVLVIVAIAKTPRLQTLTNLFIMSLASADLVMGLLVVPFGATIVVWGRWEYGSFFCELWTS |
| Human β1 | 69 | VLLIVaGNVLVIVAIAKTPRLQTLTNLFIMSLASADLVMGLLVVPFGATIVVWGRWEYGSFFCELWTS |
| Human β3 | 48 | VLaTVGGNLLVIVAIAwTPRLQTmTNVFVTSLAaADLVMGLLVVPPaATLALTGHWPLGATGCELWTS |
| Rat β3 | 48 | TVGGNLLVItAIArTPRLQTiTNvFVTSLAtADLVvGLLVmPPgATLALTGHWPLGATGCELWTS |
| | | ▬▬▬▬▬▬▬▬▬▬ |
| | | II |

| | | | |
|---|---|---|---|
| Human β2 | 112 | IDVLCVTASIETLCVIAVDRYfAITSPFKsQSLLTKNKARViILMVWIVSGLTSFLPIQMHWYR ATH |
| Rat β2 | 112 | IDVLCVTASIETLCVIAVDRYvAITSPFKYQSLLTKNKARVvILMVWIVSGLTSFLPIQMHWYR ATH |
| Rat β1 | 137 | VDVLCVTASIETLCVIALDRYLAITlPFRYQSLLTRARARaLVCTVWAISALVSFLPILMHWWRAESD |
| Human β1 | 137 | VDVLCVTASIETLCVIALDRYLAITsPFRYQSLLTRARARgLVCTVWAISALVSFLPILMHWWRAESD |
| Human β3 | 116 | VDVLCVTASIETLCALAVDRYLAVTNPLRYGaLVTKRcARtAVVLVWvVSAaVSFAPIMSQWWRVGAD |
| Rat β3 | 113 | VDVLCVTASIETLCALAVDRYLAVTNPLRYGtLVTKRrARaAVVLVWiVSAtVSFAPIMSQWWRVGAD |
| | | ▬▬▬▬▬▬▬▬ ▬▬▬▬▬▬▬▬ |
| | | III IV |

FIG. 1A

| | | | V |
|---|---|---|---|
| Human β2 | 179 | qeAInCYAnETCCDFFTNQAYAIASSIVSFYVPLViMVFVYSRVFQeAKRQLQKIDKSEGRF | |
| Rat β2 | 179 | kqAIdCYAkETCCDFFTNQAYAIASSIVSFYVPLVvMVFVYSRVFQvAKRQLQKIDKSEGRF | |
| Rat β1 | 204 | DEARRCYNDPKCCDFVTNRAYAIASSVVSFYVPLCIMAFVYLRVFREAQKQVKKIDSCERRFLtGPpR | |
| Human β1 | 204 | DEARRCYNDPKCCDFVTNRAYAIASSVVSFYVPLCIMAFVYLRVFREAQKQVKKIDSCERRFLgGPaR | |
| Human β3 | 184 | AEAQRCHSNPRCCaFASNMPYvLLSSSVSFYLPLLVMLFVYARVFVVAtRQiRlIRgELGRF PPEES | |
| Rat β3 | 181 | AEAQeCHSNPRCCsFASNMPYaLLSSSVSFYLPLLVMLFVYARVFVVAkRQrRfVRELGRF PPEES | |

| | | | | VI |
|---|---|---|---|---|
| Human β2 | 241 | QVEQHvQNLSQVEQDGRtGHGLRrS | SnFCLKEHKALKTLGIIMGTFTLCWLP | |
| Rat β2 | 241 | HaQNLSQVEQDGRSGHGLRSS | SkFCLKEHKALKTLGIIMGTFTLCWLP | |
| Rat β1 | 272 | PPSPaPSP sPGPPRPA dSLANGRSSKRRPSRLVALREQKALKTLGIIMGVFTLCWLP | | |
| Human β1 | 272 | PPSPsPSPvpAPAPpGPPPRPAaaaatAPlANGRAgKRRPSRLVALREQKALKTLGIIMGVFTLCWLP | | |
| Human β3 | 251 | PPaPS RSlAPAP VGTcAPpeGVPACGRRPARLLPLREHRALcTLGLIMGtFTLCWLP | | |
| Rat β3 | 248 | PrsPS RSpsPA tVGTptasdGVPsCGRRPARLLPLgEHRALrTLGLIMGiFsLCWLP | | |

| | | VII | |
|---|---|---|---|
| Human β2 | 289 | FFIVN IVHVIqaNLirKEVYILLNWiGYVNSgFNPLIYCRSPDFRIAFQELLC | LRR SS |
| Rat β2 | 289 | FFIVN IVHVIrdNLIPKEVYILLNWLGYVNSAFNPLIYCRSPDFRIAFQELLC | LRR SS |
| Rat β1 | 329 | FFLAN VKAFHRdLVPDRLFVFFNWLGYANSAFNPIIYCRSPDFRKAFQrLLCCARRAcRRR AaH |
| Human β1 | 340 | FFLAN VKAFHReLVPDRLFVFFNWLGYANSAFNPIIYCRSPDFRKAFQgLLCCARRAA RRRhAtH |
| Human β3 | 308 | FFLANVLRALgGPSLVPgpaFlALNWLGYANSAFNPLIYCRSPDFRsAFRRLLC rcGRR |
| Rat β3 | 305 | FFLANVLRALvGPSLVPsgvFiALNWLGYANSAFNPLIYCRSPDFRdAFRRLLC syGgR |

FIG. 1B

```
Human    β2  347  lKaYGNGYSSN          gnTGEQ  YhveQEKENKlLCEdlPGtEdFVghQGTVPSdnIDSQGRNCsTN
Rat      β2  347  sKtYGNGYSSNsnGrtdyTGEQSaYqlgQEKENeLLCEeaPGmEGFVncQGTVPSlSIDSQGRNCnTN
Rat      β1  395  GDRPRASGCLARaGPPPSPGApSDDDDDD aGATPPARLLEPWAGCNGGttTVDSDSSLDEPgRgGFs
Human    β1  406  GDRPRASGCLARPGPPPSPGAaSDDDDDDvvGATPPARLLEPWAGCNGG AaaDSDSSLDEPcRpGFa
Human    β3  367  lPpEPcaaARPalFPS           GvPA         arsspAqprlcqrlDgvtgaegp
Rat      β3  364      gPeEP        RvvtFPaspvasrqnsplnrfdGyegerpfpt Human    β2  409  DS1L
Rat      β2  404  DSpL
Rat      β1  457  SESKV
Human    β1  468  SESKV
Human    β3  402  a
Rat      β3
```

```
Met Ala Pro Trp Pro His Lys Asn Gly Ser Leu Ala Phe Trp Ser Asp
  1                   5                  10                  15
Ala Pro Thr Leu Asp Pro Ser Ala Ala Asn Thr Ser Gly Leu Pro Gly
                 20                  25                  30
Val Pro Trp Ala Ala Leu Ala Gly Ala Leu Leu Ala Leu Ala Thr
         35                  40                  45
Val Gly Gly Asn Leu Leu Val Ile Thr Ala Ile Ala Arg Thr Pro Arg
     50                  55                  60
Leu Gln Thr Ile Thr Asn Val Phe Val Thr Ser Leu Ala Thr Ala Asp
 65                  70                  75                  80
Leu Val Val Gly Leu Leu Val Met Pro Pro Gly Ala Thr Leu Ala Leu
             85                  90                  95
Thr Gly His Trp Pro Leu Gly Ala Thr Gly Cys Glu Leu Trp Thr Ser
                100                 105                 110
Val Asp Val Leu Cys Val Thr Ala Ser Ile Glu Thr Leu Cys Ala Leu
            115                 120                 125
Ala Val Asp Arg Tyr Leu Ala Val Thr Asn Pro Leu Arg Tyr Gly Thr
        130                 135                 140
Leu Val Thr Lys Arg Arg Ala Arg Ala Ala Val Val Leu Val Trp Ile
145                 150                 155                 160
Val Ser Ala Thr Val Ser Phe Ala Pro Ile Met Ser Gln Trp Trp Arg
            165                 170                 175
Val Gly Ala Asp Ala Glu Ala Gln Glu Cys His Ser Asn Pro Arg Cys
        180                 185                 190
Cys Ser Phe Ala Ser Asn Met Pro Tyr Ala Leu Leu Ser Ser Val
    195                 200                 205
```

FIG. 6A

```
Ser Phe Tyr Leu Pro Leu Val Met Leu Phe Val Tyr Ala Arg Val
210                 215                 220
Phe Val Ala Lys Arg Gln Arg Arg Phe Val Arg Glu Leu Gly
    225                 230                 235             240
Arg Phe Pro Pro Glu Ser Pro Arg Ser Arg Ser Pro Ser
            245                 250                 255
Pro Ala Thr Val Gly Thr Pro Thr Ala Ser Asp Gly Val Pro Ser Cys
                260                 265                 270
Gly Arg Arg Pro Ala Arg Leu Leu Pro Leu Gly Glu His Arg Ala Leu
        275                 280                 285
Arg Thr Leu Gly Leu Ile Met Gly Ile Phe Ser Leu Cys Trp Leu Pro
        290                 295                 300
Phe Phe Leu Ala Asn Val Leu Arg Ala Leu Val Gly Pro Ser Leu Val
305                 310                 315                 320
Pro Ser Gly Val Phe Ile Ala Leu Asn Trp Leu Gly Tyr Ala Asn Ser
            325                 330                 335
Ala Phe Asn Pro Leu Ile Tyr Cys Arg Ser Pro Asp Phe Arg Asp Ala
                340                 345                 350
Phe Arg Arg Leu Leu Cys Ser Tyr Gly Gly Arg Gly Pro Glu Glu Pro
        355                 360                 365
Arg Val Val Thr Phe Pro Ala Ser Pro Val Ala Ser Arg Gln Asn Ser
370                 375                 380                 385
Pro Leu Asn Arg Phe Asp Gly Tyr Glu Gly Glu Arg Pro Phe Pro Thr
            390                 395                 400
```

FIG. 6B

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 400
        ( B ) TYPE: amino acid
        ( C ) STRANDEDNESS: single
        ( D ) TOPOLOGY: linear     ( i i ) MOLECULE TYPE: Polypeptide     ( x i ) SEQUENCE DESCRIPTION: SEQ ID NO:1:

```
Met  Ala  Pro  Trp  Pro  His  Lys  Asn  Gly  Ser  Leu  Ala  Phe  Trp  Ser  Asp
 1              5                      10                       15

Ala  Pro  Thr  Leu  Asp  Pro  Ser  Ala  Ala  Asn  Thr  Ser  Gly  Leu  Pro  Gly
              20                      25                       30

Val  Pro  Trp  Ala  Ala  Ala  Leu  Ala  Gly  Ala  Leu  Leu  Ala  Leu  Ala  Thr
              35                      40                       45

Val  Gly  Gly  Asn  Leu  Leu  Val  Ile  Thr  Ala  Ile  Ala  Arg  Thr  Pro  Arg
      50                      55                       60

Leu  Gln  Thr  Ile  Thr  Asn  Val  Phe  Val  Thr  Ser  Leu  Ala  Thr  Ala  Asp
 65                      70                       75                       80

Leu  Val  Val  Gly  Leu  Leu  Val  Met  Pro  Pro  Gly  Ala  Thr  Leu  Ala  Leu
                  85                      90                       95

Thr  Gly  His  Trp  Pro  Leu  Gly  Ala  Thr  Gly  Cys  Glu  Leu  Trp  Thr  Ser
                 100                     105                      110

Val  Asp  Val  Leu  Cys  Val  Thr  Ala  Ser  Ile  Glu  Thr  Leu  Cys  Ala  Leu
              115                     120                      125

Ala  Val  Asp  Arg  Tyr  Leu  Ala  Val  Thr  Asn  Pro  Leu  Arg  Tyr  Gly  Thr
     130                      135                     140

Leu  Val  Thr  Lys  Arg  Arg  Ala  Arg  Ala  Ala  Val  Val  Leu  Val  Trp  Ile
145                      150                     155                      160

Val  Ser  Ala  Thr  Val  Ser  Phe  Ala  Pro  Ile  Met  Ser  Gln  Trp  Trp  Arg
              165                     170                      175

Val  Gly  Ala  Asp  Ala  Glu  Ala  Gln  Glu  Cys  His  Ser  Asn  Pro  Arg  Cys
              180                     185                      190

Cys  Ser  Phe  Ala  Ser  Asn  Met  Pro  Tyr  Ala  Leu  Leu  Ser  Ser  Ser  Val
          195                     200                     205

Ser  Phe  Tyr  Leu  Pro  Leu  Leu  Val  Met  Leu  Phe  Val  Tyr  Ala  Arg  Val
     210                      215                     220

Phe  Val  Val  Ala  Lys  Arg  Gln  Arg  Arg  Phe  Val  Arg  Arg  Glu  Leu  Gly
225                      230                     235                      240

Arg  Phe  Pro  Pro  Glu  Glu  Ser  Pro  Arg  Ser  Pro  Ser  Arg  Ser  Pro  Ser
```

|     | 245 |     |     |     |     | 250 |     |     |     |     | 255 |     |     |
|-----|-----|-----|-----|-----|-----|-----|-----|-----|-----|-----|-----|-----|-----|
| Pro | Ala | Thr | Val 260 | Gly | Thr | Pro | Thr | Ala 265 | Ser | Asp | Gly | Val | Pro 270 | Ser | Cys |
| Gly | Arg | Arg 275 | Pro | Ala | Arg | Leu | Leu 280 | Pro | Leu | Gly | Glu | His 285 | Arg | Ala | Leu |
| Arg | Thr 290 | Leu | Gly | Leu | Ile | Met 295 | Gly | Ile | Phe | Ser | Leu 300 | Cys | Trp | Leu | Pro |
| Phe 305 | Phe | Leu | Ala | Asn | Val 310 | Leu | Arg | Ala | Leu | Val 315 | Gly | Pro | Ser | Leu | Val 320 |
| Pro | Ser | Gly | Val | Phe 325 | Ile | Ala | Leu | Asn | Trp 330 | Leu | Gly | Tyr | Ala | Asn 335 | Ser |
| Ala | Phe | Asn | Pro 340 | Leu | Ile | Tyr | Cys | Arg 345 | Ser | Pro | Asp | Phe | Arg 350 | Asp | Ala |
| Phe | Arg | Arg 355 | Leu | Leu | Cys | Ser | Tyr 360 | Gly | Gly | Arg | Gly | Pro 365 | Glu | Glu | Pro |
| Arg | Val 370 | Val | Thr | Phe | Pro | Ala 375 | Ser | Pro | Val | Ala | Ser 380 | Arg | Gln | Asn | Ser |
| Pro 385 | Leu | Asn | Arg | Phe | Asp 390 | Gly | Tyr | Glu | Gly | Glu 395 | Arg | Pro | Phe | Pro | Thr 400 |

CLONED CELL LINE EXPRESSING RAT $\beta_{3A}$ ADRENERGIC RECEPTOR

TECHNICAL FIELD

This application relates to fat cell specific $\beta$-adrenergic receptors from brown adipose tissue and clone cells related to the receptor.

BACKGROUND OF THE INVENTION

There has long been an interest in the structure of adipose tissue as it relates to a possible role in obesity. Brown adipose tissue is the main effector of cold- and diet-induced thermogenesis in mammals, such as rodents. See Foster et al., Can. J. Physiol., Vol. 56, 110 (1978) or Rothwell et al., Nature (London), Vol. 281, 31 (1979). The process of thermogenesis can represent a major expenditure of energy and play an important role in overall energy balance. Because brown adipose tissue has been demonstrated in humans of all ages and is often atrophied or quiescent in obese animals, much interest has recently been directed towards development of compounds that stimulate the thermogenesis metabolic response as possible anti-obesity agents.

Brown adipose tissue metabolism is primarily controlled by norepinephrine released from the sympathetic nerve terminals that act through $\beta$-adrenergic receptors. Both $\beta_1$- and $\beta_2$-adrenergic receptor subtypes are present in rat brown adipose tissue; however, pharmacological studies with novel thermogenic $\beta$-adrenergic agonists have suggested the existence of an atypical $\beta$-adrenergic receptor in the brown adipose tissue that mediates lipolysis (breakdown of fat). Parallel studies have also suggested the presence of atypical $\beta$-adrenergic receptors with similar pharmacological properties in white adipose tissue, the digestive track, and in skeletal muscle.

Accordingly, there is a need in the art for isolation and understanding of the fat cell $\beta$ receptor or receptors which are related to the thermogenesis process. Such an isolation of the $\beta$-adrenergic receptor(s) would allow for the diagnosis of obesity, the treatment of obesity, the testing of medications for their effectiveness in stimulating the thermogenesis metabolic response in obesity patients.

DISCLOSURE OF THE INVENTION

An object of the invention relates to obtaining the sequence of a $\beta$-adrenergic receptor polypeptide that mediates lipolysis and which is produced by $\beta$-adrenergic fat cell receptor clones.

Another object of the present invention is to produce clone cells coding for fat cell $\beta$-adrenergic polypeptide receptors that mediate lipolysis.

A further object of the invention is to choose several clonal cell lines that permanently express the fat cell $\beta$ receptor, which mediate lipolysis, and choose one of the cell lines for additional pharmacological and biochemical characterization.

A further object of the invention is to provide a diagnostic test for determining decreased levels of the fat cell $\beta$-adrenergic receptor that mediates lipolysis in order to diagnose obesity caused by less active lipolysis.

DESCRIPTION OF THE INVENTION PREFERRED EMBODIMENTS

The present invention relates to a fat cell specific $\beta$-adrenergic receptor that mediates lipolysis. Particularly preferred is a $\beta$-adrenergic receptor polypeptide having a sequence according to SEQ ID NO: 1.

The present invention also provides cloned cells encoding for a fat cell $\beta$-adrenergic receptor that mediates lipolysis. Further provided is a clone cell which is obtained by cotransfection of CHO cells. More preferred are clone cells which produce a $\beta_{3A}$-adrenergic receptor. Even more preferred are clone cells which produce an adrenergic receptor having the sequence according to SEQ ID NO: 1.

The invention still further provides a diagnostic test for determining decreased levels of fat cells $\beta$-adrenergic receptors that mediate lipolysis in order to diagnose obesity caused by less active lipolysis. More preferred is a diagnostic test for determining decreased levels of a $\beta$-adrenergic receptor polypeptide having a sequence according to SEQ ID NO: 1.

EXPERIMENTAL

A rat interscapular brown adipose tissue (IBAT) cDNA library was cloned and probed with DNA probes encoding human $\beta_1$- and rat $\beta_2$-adrenergic receptors under conditions of low stringency. Nine positive clones were identified that were demonstrated by restriction mapping to be different from rat $\beta_1$ and $\beta_2$ adrenergic receptor cDNAs. Sequence analysis of these clones reveal the presence of a single opening reading frame of 1,200 bp encoding a polypeptide of about 400 amino acids with a predicted size of 43,169 daltons.

Figure 1B:
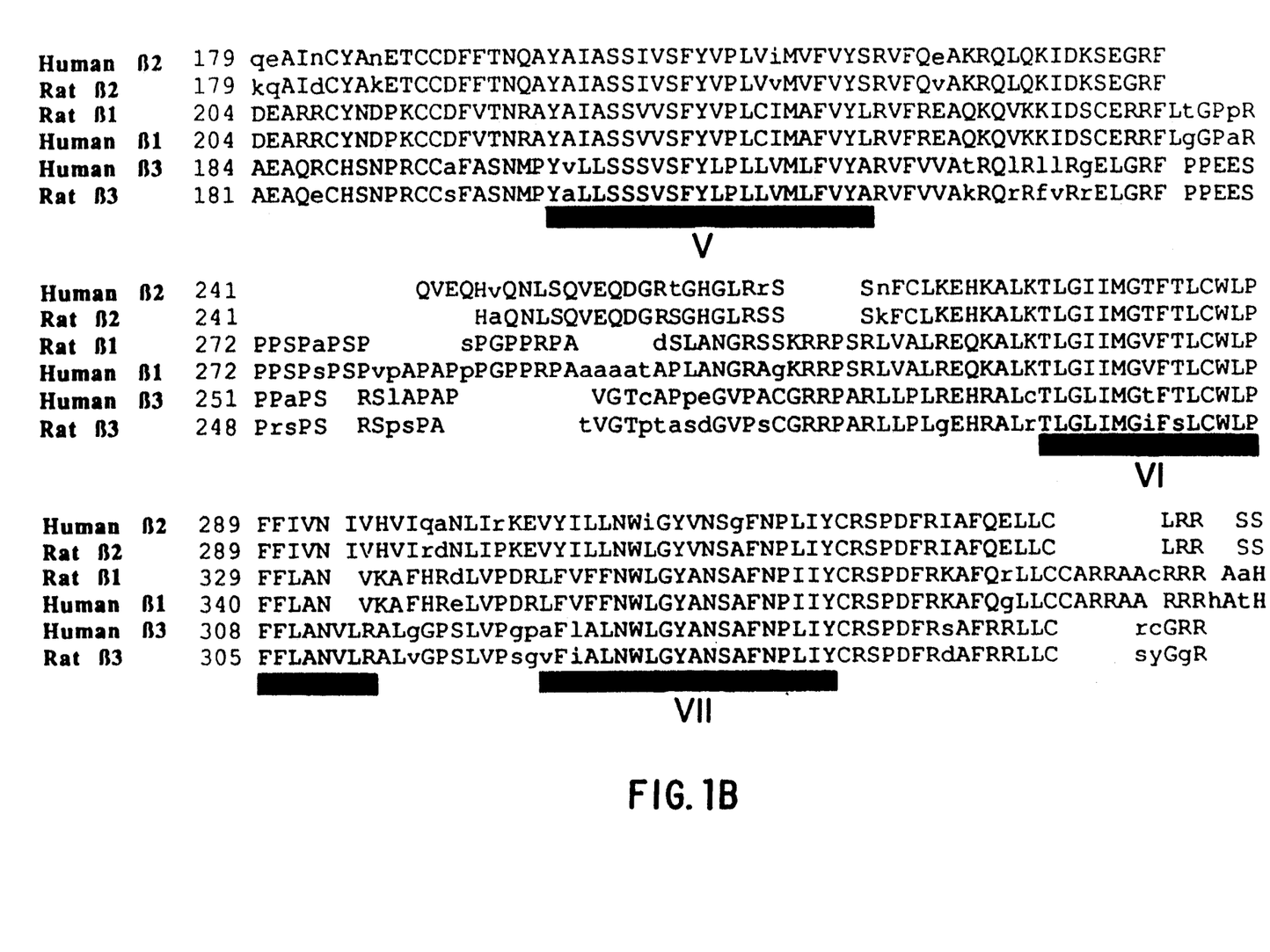
FIG. 1 relates to a comparison of adrenergic receptor polypeptides of humans and rats. This figure shows human $\beta$-2, rat $\beta$-2, rat $\beta$, human $\beta$-1, human $\beta$-3 and rat $\beta$-3 receptor sequences.
Figure 1C:
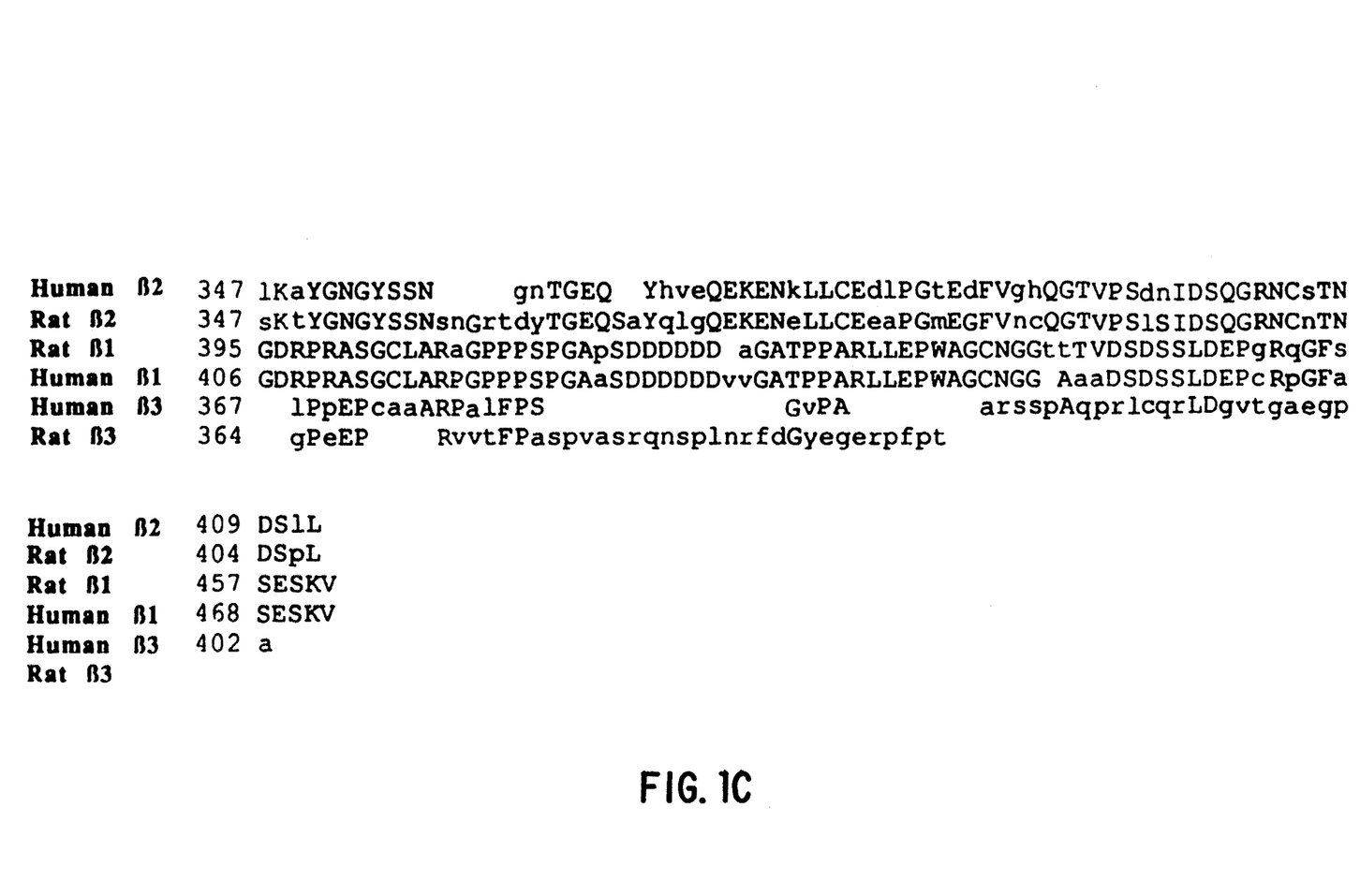

The adipose tissue $\beta$-adrenergic receptor has 49% and 40% identity, respectively to rat $\beta_1$- (C. A. Machida et al, J. Biol. Chem. 265, 12960 (1990)) and $\beta_2$-adrenergic receptors (D. A. Robinson, thesis, State University of New York at Buffalo (1988)) and 80% identity to the human $\beta_3$-adrenergic receptor (L. J. Emorine et al, Science 245, 1118 (1989)) (FIG. 1).

Sequence identity between $\beta_1$- and $\beta_2$-adrenergic receptors from rats (C. A. Machida et al, J. Biol. Chem. 265, 12960 (1990); D. A. Robinson, Thesis, State University of New York at Buffalo (1988)) and humans (T. Frielle et al, Proc. Natl. Acad. Sci. U.S.A. 84, 7920 (1987); F. Z. Chung et al, FEBS Lett. 211, 200 (1987)) is extremely high: 90% for $\beta_1$-adrenergic receptors and 87% for $\beta_2$-adrenergic receptors.

While the rat adipose tissue $\beta$-adrenergic receptor is more closely related to the human $\beta_3$-adrenergic receptor than to either rat $\beta_1$- or $\beta_2$-adrenergic receptor subtypes, the amino acid identity is lower than might be expected for species differences alone. Because of the high homology between this receptor and the human $\beta_3$-adrenergic receptor, its unique pharmacological properties and fat cell specificity, we have defined this novel receptor as a $\beta_{3A}$(adipose)adrenergic subtype.

The $\Theta_{3A}$-adrenergic receptor exhibits several structural features common to G protein-coupled receptors. It contains seven regions of hydrophobic sequence that are presumed to represent transmembrane spanning domains (FIG. 1). There are two putative sites of N-linked glycosylation (N-X-S/T) in the amino terminus and several serine and threonine residues in the COOH terminus and in the third intracellular loop that may serve as sites for regulation by protein kinases.

Furthermore, the $\Theta_{3A}$-receptor contains several conserved amino acids at positions $Asp^{80}$, $Asp^{114}$, $Asp^{131}$, $Cys^{107}$, $Cys^{186}$, $Cys^{192}$, $Cys^{193}$, $Ser^{209}$, that have been demonstrated to play important roles in $\beta$-adrenergic receptor-ligand interactions and receptor activation by agonists (R. A. F. Dixon et al, Cold Spring Harbor Symp. Quant. Biol. 53, 487 (1988); J. C. Venter et al, Biochem. Pharmacol. 38, 1197 (1989); C. M. Fraser, J. Biol. Chem., 264, 9266 (1989); C. F. Strader, I. S. Sigal and R. A. F. Dixon, FASEB J. 3, 1825 (1989)).

Using a protocol for cotransfection of CHO cells (a 1.5 kb fragment was excised from pBluescript using SacI (present in the multiple cloning site of the vector) and BamHI and inserted into the Sac/BamH/sites of PSVL (Pharmacie). CHO-K1 cells were cotransfected with pSVL and pMSVneo (neomycin resistance plasmid) F. Z. Chung, C. D. Wang, P. C. Potter, J. C. Venter and C. M. Fraser, J. Biol. Chem. 263, 4052 (1988) using the CaPO$_4$ precipitation technique. Stable transfectants were obtained by growth of the cells in culture medium containing Geneticin (500 $\mu$g/ml); colonies derived from single cells were isolated and expanded.

Because atypical $\beta$-adrenergic receptors in adipose tissue display low affinity for $\beta$-adrenergic antagonists, cell lines were screened for the expression of $\beta$-adrenergic receptors by measuring isoproterenol ($10^{-6}$M)-mediated increases in intracellular cAMP.), we obtained several clonal cell lines that permanently express the fat cell $\beta$ receptor and chose one for additional pharmacological and biochemical characterization. Membranes from transfected CHO cells display saturable binding of the radioligand, [$^{125}$I]-iodocyanopindolol ([$^{125}$I]-ICYP) (Transfected cell membranes were prepared by lysis of cells in hypotonic solution containing 5 mM NAPO$_4$, pH 7.4, 2 mM MgSO$_4$ followed by centrifugation at 1000$\times$g for 5 minutes to remove intact cells and cell nuclei. The supernatant was centrifuged at 40,000$\times$g for 30 minutes to collect the membrane fraction.

Membrane associated $\beta$-adrenergic receptors (3–6 $\mu$g protein) were labeled with increasing concentrations of [$^{125}$I]-CYP in the presence and absence of 10 $\mu$M 1C1 118,551 by incubation at 37° C. for 30 minutes in Hank's buffer in a final volume of 250 $\mu$l. Incubations were terminated by filtration over Whatman GF/C glass fiber filters using a Brandel cell harvester. Scatchard analysis of saturation isotherms was performed to yield estimates of $K_D$ (equilibrium dissociation constant for [$^{125}$I]-CYP) and $B_{max}$ (total number of binding sites). The $K_D$ value was utilized in computer analysis of competition displacement curves.) The calculated equilibrium dissociation constant ($K_D$) for [$^{125}$I]-ICYP binding is 1.3$\pm$0.4 nM, a value significantly greater than $K_D$ values for [$^{125}$I]-ICYP binding to $\beta_1$-(11 pM) (13) and $\beta_2$-adrenergic receptors (30 pM) (D. A. Robinson, thesis, State University of New York at Buffalo (1988)) but similar to that reported for [$^{125}$I]-ICYP binding to the $\beta_3$-adrenergic receptor (0.5 nM) (L. J. Emorine et al, Science 245, 1118 (1989)). The density of $\beta$-adrenergic receptors expressed in this cell line is 1100$\pm$187 fmol/mg membrane protein.

Figure 2:
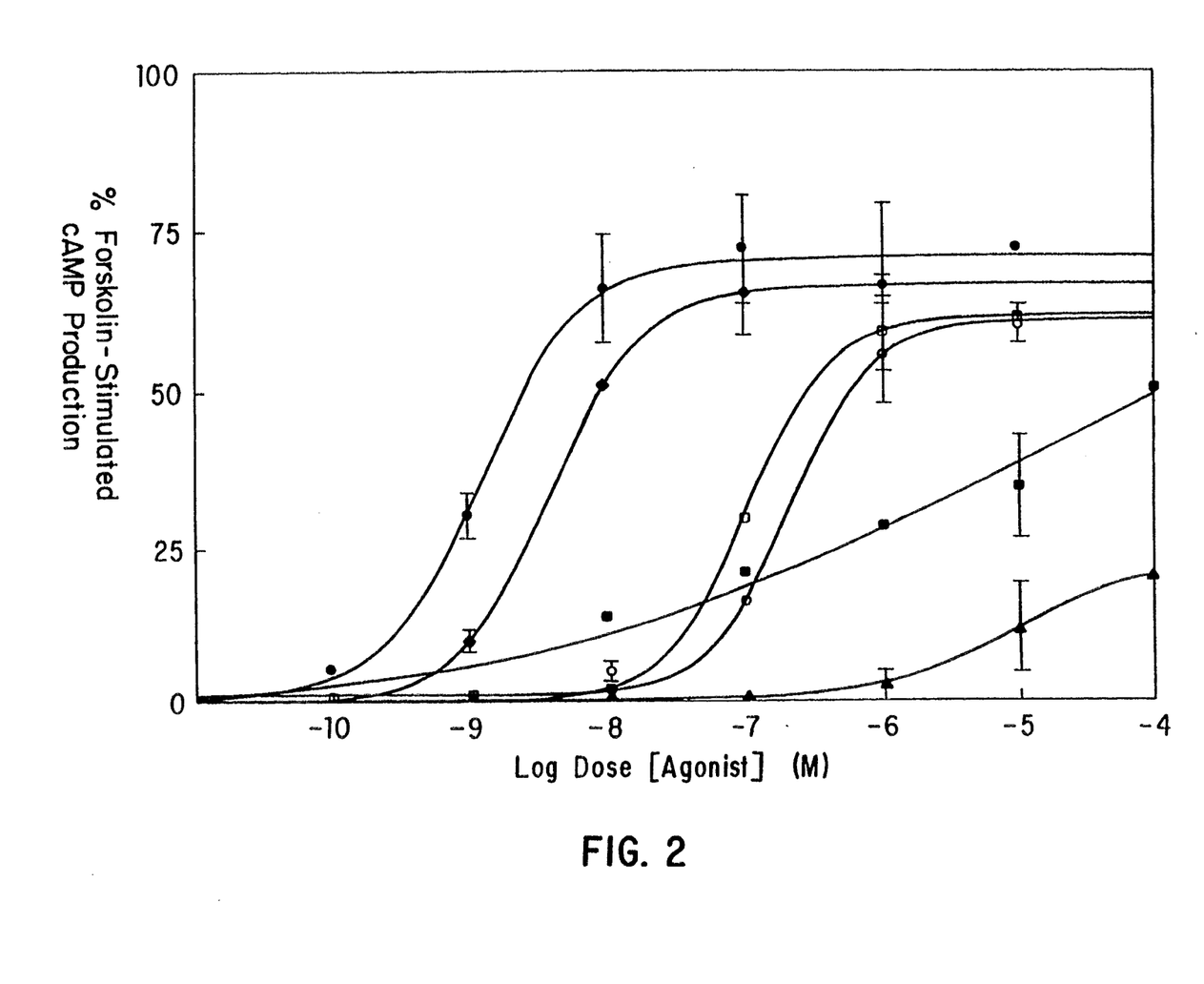
FIG. 2 relates to the percent of Forskolin-stimulated cAMP production in transfected CHO cells expressing the fat cell $\beta$ receptor according to the present invention with a rank order of potency of agonists BRL 37344→isoproterenol→norepinephrine→epinephrine→zinterol→tazolol.
Figure 3:
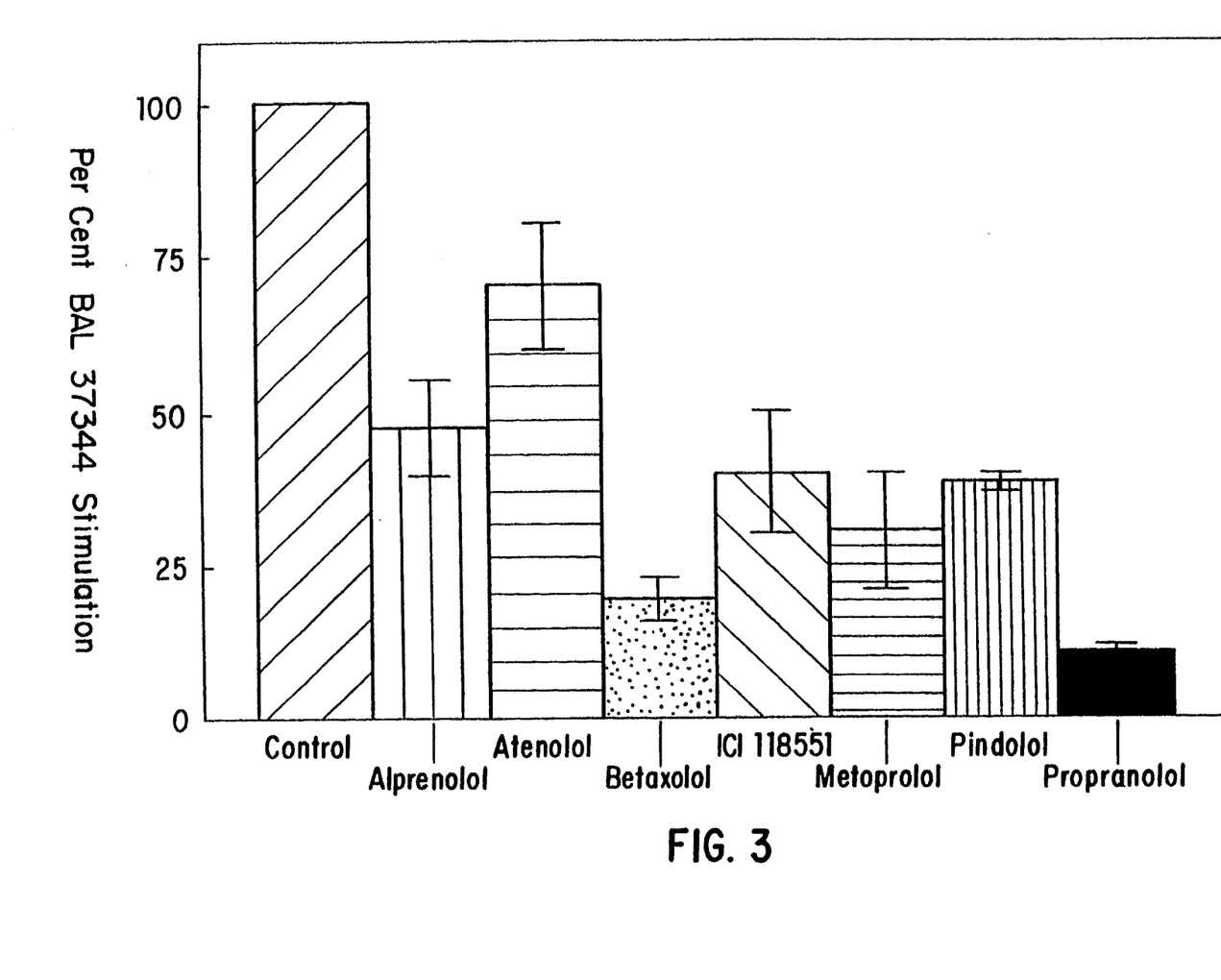
FIG. 3 relates to the potency of antagonists (at $10^{-4}$M concentrations) for inhibiting BRL 34344-induced cAMP accumulation in transfected CHO cells for several antagonists.

Agonists produce dose-dependent increases in intracellular cAMP concentrations in transfected CHO cells with a rank order of potency of BRL 37344>isoproterenol>norepinephrine>epinephrine>zinterol>tazolol (FIG. 2, Table 1) (21). $K_{act}$ values for BRL 37344 and isoproterenol-mediated increases in intracellular cAMP in transfected CHO cells are in very good agreement with the EC$_{50}$ values for increases in lipolysis in brown adipocytes as described by Arch et al. (7); i.e., 1.3 and 1.7 nM for BRL 37344 and 4.0 and 8.0 nM for isoproterenol in transfected cells and brown adipocytes, respectively. The greater potency of norepinephrine as compared with epinephrine suggests that receptor activation in vivo is most likely mediated through sympathetic innervation. Antagonists (at $10^{-4}$M concentrations) display an order of potency for inhibition of BRL 37344-induced cAMP accumulation in transfected CHO cells of propranolol (89% inhibition)>betaxolol (80% inhibition)>metoprolol (70% inhibition)>pindolol (61% inhibition)=118,51 (60% inhibition)>alprenolol (52% inhibition)>atenolol (30% inhibition) (FIG. 3).

In competition displacement studies (For competition displacement studies, membranes (containing 3–4 fmol [$^{125}$I]-ICYP binding sites were incubated with [$^{125}$I]-CYP or [$^3$H]-CGP 12177 ($\sim$1$\times$K$^D$ concentration) plus a range of concentrations of competing ligands. Competition displacement curves were analyzed according to a mass action model for receptor-ligand interactions using a computerized interactive non-linear least squares curve-fitting program (GraphPAD INPLOT, San Diego, Calif.).

Competition displacement experiments were performed at least 3 times in triplicate. Triplicate values from each experiment were averaged and nonlinear regression was performed on data averaged from all competition displacement curves for a given ligand), agonists display a rank order of potency of BRL 37344 (atypical $\beta$-adrenergic agonist)>>zinterol ($\beta_2$-adrenergic agonist)>tazolol ($\beta_1$-adrenergic agonist)>($-$) isoproterenol>epinephrine>norepinephrine>(+) isoproterenol (Table 1).

The relative affinities of BRL 37344 and ($-$) isoproterenol for displacement of [$^3$H]-CGP 12177 are similar to those observed with [$^{125}$I]-ICYP. Antagonists display a rank order of potency of alprenolol>propranolol>ICI 118,551 (β$_2$-adrenergic selective)>betaxolol (β$_1$-adrenergic selective) (Table 1). The ⊖$_{3A}$-adrenergic receptor exhibits a markedly lower affinity for classical β-adrenergic antagonists than either β$_1$- or β$_2$-adrenergic receptor subtypes.

The pharmacological properties of the ⊖$_{3A}$-adrenergic receptor differ significantly from those reported by Emorine et al. (Science 245, page 1118 (1989) for a human β$_3$-receptor expressed in CHO cells. The rank order of agonist potency for inhibition of [$^{125}$I]-ICYP binding to the β$_3$-adrenergic receptor is BRL 37344>norepinephrine>(−)a isoproterenol>>(+) isoproterenol>epinephrine (11) as compared with BRL 37344>>(−) isoproterenol>epinephrine>norepinephrine>(+) isoproterenol for the β$_{3A}$-adrenergic receptor.

The pharmacological profile of the ⊖$_{3A}$-receptor does not agree with the human β$_3$-receptor. (L. J. Emorine et al, Science 245, 1118 (1989)). Also, it does not agree with any known tissue pharmacology, nor is it consistent with the pharmacological definition of a β-adrenergic receptor (isoproterenol more potent than either epinephrine or norepinephrine). In addition, most of the classical non-selective β-adrenergic antagonists do not inhibit [$^{125}$I]-ICYP binding to the β$_3$-adrenergic receptor (L. J. Emorine et al, Science 245, 1118 (1989)). Therefore, it is clear that there are substantial pharmacological differences between the fat cell ⊖$_{3A}$-adrenergic receptor and the receptor described by Emorine et al. (L. J. Emorine et al, Science 245, 1118 (1989)).

The distribution of β-adrenergic receptor subtypes was determined as follows.

To further investigate the distribution of β-adrenergic receptor subtypes, poly (A) RNAs from various tissues were isolated and fractionated on a formaldehyde-agarose gel (FIG. 4) (Fifteen μg of poly (A)+ RNA from rat IBAT, epididymal white adipose tissue, brain, heart, ileum, liver and lungs were electrophoresed in an agarose gel containing formaldehyde as described [H. Lehrach, D. Diamond, J. M. Wozney, H. Boedtker, Biochem. 16, 4743 (1977)] and transferred to Gene Screen Plus membranes (Dupont/New England Nuclear) by capillary blotting. Rat β$_1$-adrenergic receptor (Venter et al, unpublished), rat β-adrenergic receptor (J. Gocayne et al, Proc. Natl. Acad. Sci. U.S.A. 84, 8296 (1987) and rat ⊖$_{3A}$-adrenergic receptor cDNAs were labeled by random priming with [α-$^{32}$P]-dCTP (Dupont/New England Nuclear) to specific activities of ~1×10$^9$ dpm/μg DNA. RNA blots were hybridized overnight at 42° C. in 45% formamide and 4×SSC (0.6M NaCl, 0.06M Na citrate) and then washed sequentially in a solution of 0.1×SSC, 0.1% sodium dodecyl sulfate at 55° C. for 15 minutes followed by 60° C. for 15 minutes.

Figure 4A:
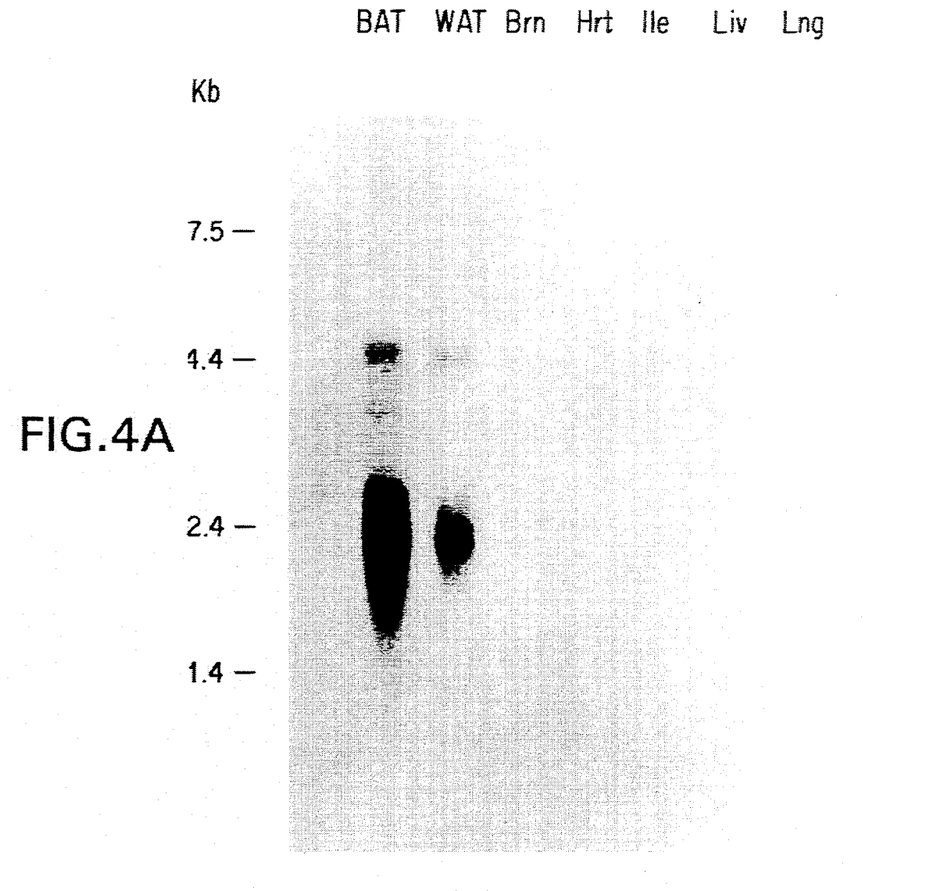
FIG. 4 shows the distribution of $\beta$-adrenergic receptor sub-types poly(A)+ RNAs from various tissues which were isolated and fractionated on a formaldehyde-agarose gel. The tissues were brown adipose tissue (BAT), white adipose tissue (WAT), brain (Brn), heart (Hrt), ileum (Ile), liver (Liv), or lung (Lng).
Figure 4B:
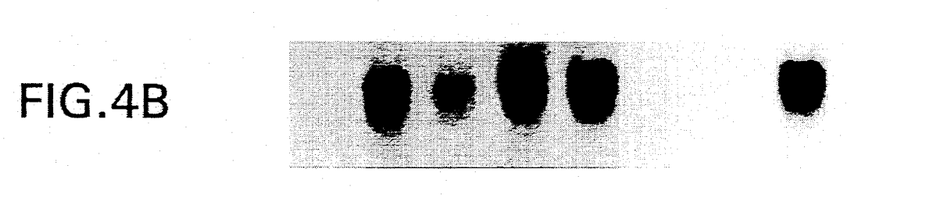
Figure 4C:
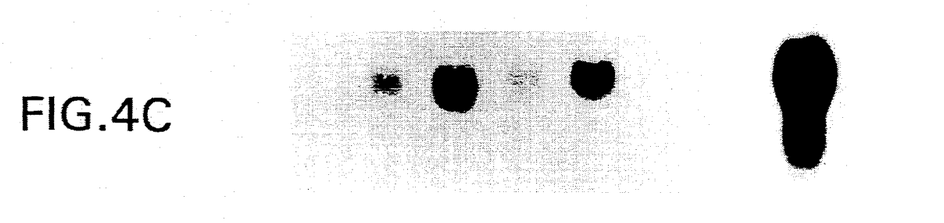

Size estimates of RNA species were established by comparison with an RNA ladder. An mRNA species is detected at 3.1 kb with the β$_1$-adrenergic receptor probe, at 2.3 kb with the β$_2$-adrenergic receptor probe and at 2.3 kb with the β$_{3A}$-adrenergic receptor probe. Minor bands at 2.8, 3.8 and 4.6 kb are also detected with the β-$_{3A}$-adrenergic receptor probe. As a control, an oligo (dT)$_{12-18}$ probe was labeled with [γ$^{32}$P]-TTP using T4 polynucleotide kinase. Densitometric analysis of autoradiograms was performed with a high resolution densitometer. The values of the β-adrenergic receptor signals were normalized for the amount of poly (A)+RNA on the membranes with the corresponding oligo (dT) signal.

From the above experimentation, the distribution of β-adrenergic receptor subtypes in various tissues is as follows. β$_1$-adrenergic receptor mRNA is present in brown and white adipose tissue, brain, heart and lung. β$_2$-adrenergic receptor mRNA is also present in these tissues; however, with the exception of the lung, it is present at significantly lower levels. The β$_{3A}$-adrenergic receptor mRNA is abundant in brown adipose tissue, with no ⊖$_{3A}$-receptor specific mRNA detectable in brain, heart, ileum, liver or lung. White adipose tissue from rat (FIG. 4) and human (data not shown) also contains an mRNA that hybridizes strongly with the ⊖$_{3A}$-receptor cDNA probe.

It has been difficult to quantitate the atypical β-adrenergic receptor in adipose tissue since radiolabeled antagonists commonly used display significantly (up to 100-fold) greater affinities for β$_1$- and β$_2$-adrenergic receptor subtypes than for the atypical β-adrenergic receptor. However, under identical conditions using probes of similar specific activities, it was estimated that the ⊖$_{3A}$-receptor mRNA is present in a 5-fold and 4-fold excess over β$_1$-receptor mRNA in brown and white adipose tissue, respectively, whereas β$_2$-receptor mRNA is virtually undetectable (data not shown). Thus, the relative amounts of receptor subtype-specific mRNA species suggest that the ⊖$_{3A}$-adrenergic receptor, which is presumed to mediate lipolysis (U. R. S. Arch et al, Nature (London) 309, 163 (1984)), is the predominant β-receptor in adipose tissue.

Further to the above experimentation to determine receptor distribution and its effects on obesity, the following relates to normal vs. abnormalities in brown adipose tissue.

Numerous investigations have reported abnormalities in brown adipose tissue of heredity obese animals (J. Himms-Hagen, Prog. Lip. Res. 28, 67 (1989)). In both obese (ob/ob) mice and (fa/fa) Zucker rats, the thermogenic response of brown adipose tissue to sympathetic stimulation is decreased as compared with lean controls (F. Assimacopoulos-Jeannet, J. P. Giacobino, J. Seydoux, L. Girardier, B. Jeanrenaud, Endocrinol. 110, 439 (1982); A. Marette, A. Geloen, A. Collett and J. Bukowiecki, Am. J. Physiol. 258, E320 (1990)). In obese (fa/fa) Zucker rats, β-adrenergic stimulation of adenylate cyclase is also reduced (P. Muzzin, J. P. Revelli, D. Ricquier, M. K. Meier, F. Assimacopoulos-Jeannet, J. P. Giacobino, Biochem. J. 261, 721 (1989)).

Figure 5:
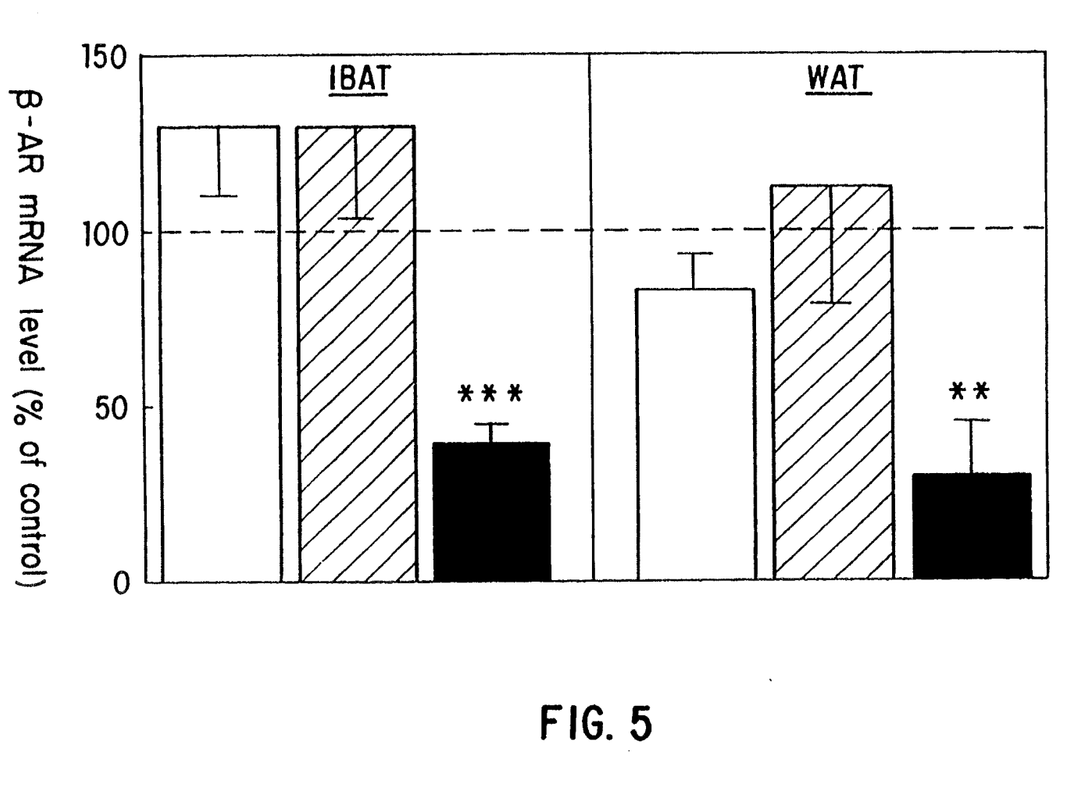
FIG. 5 compares the level of $\beta_1$, $\beta_2$ and $\beta_{3A}$-adrenergic receptor mRNA levels in brown and white fat of obese rats as compared to lean controls. The dotted line represents 100% as the amount of adrenergic receptor found in the lean rat. The white histogram box represents the $\beta_1$ receptor, the diagonally cross-hatched histogram box represents the $\beta_2$ receptor and the darkened histogram box represents the level of $\beta_{3A}$-adrenergic receptor mRNA.
Figure 6A:
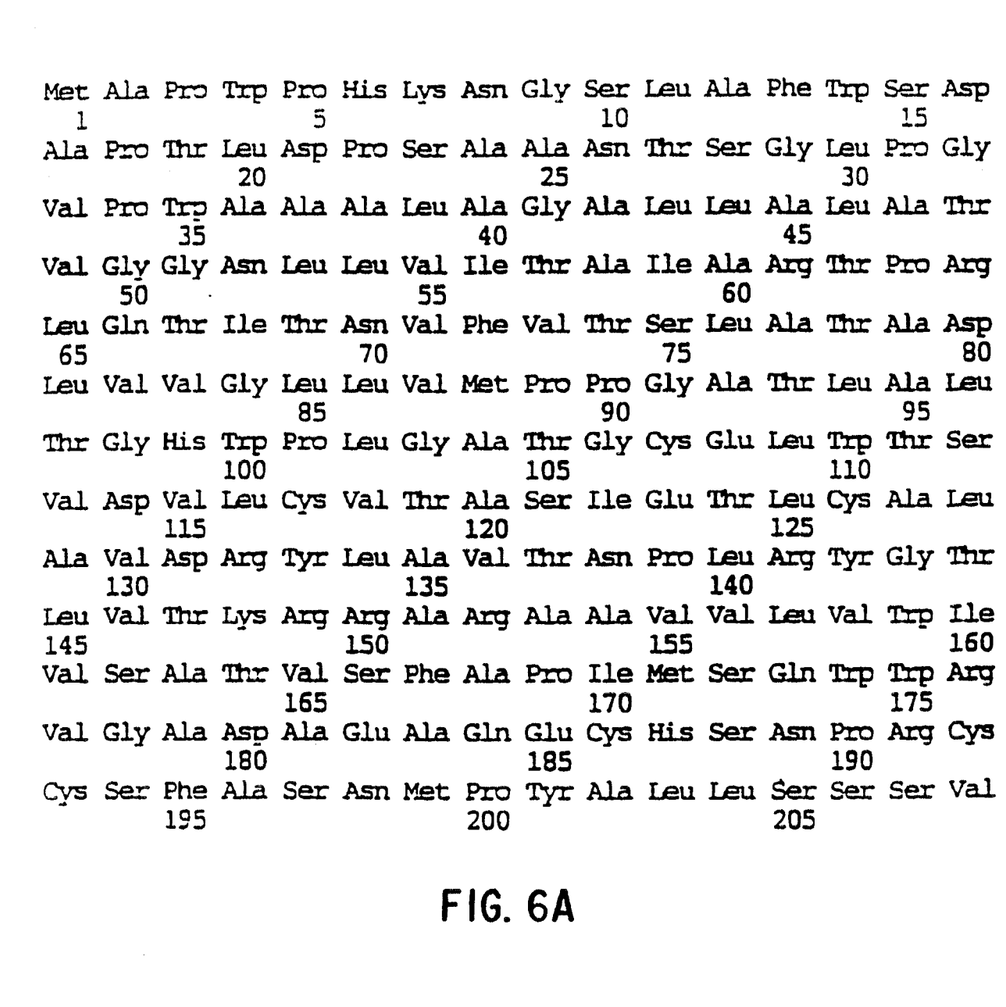
FIG. 6 relates to a polypeptide having a sequence according to SEQ ID NO:1.
Figure 6B:
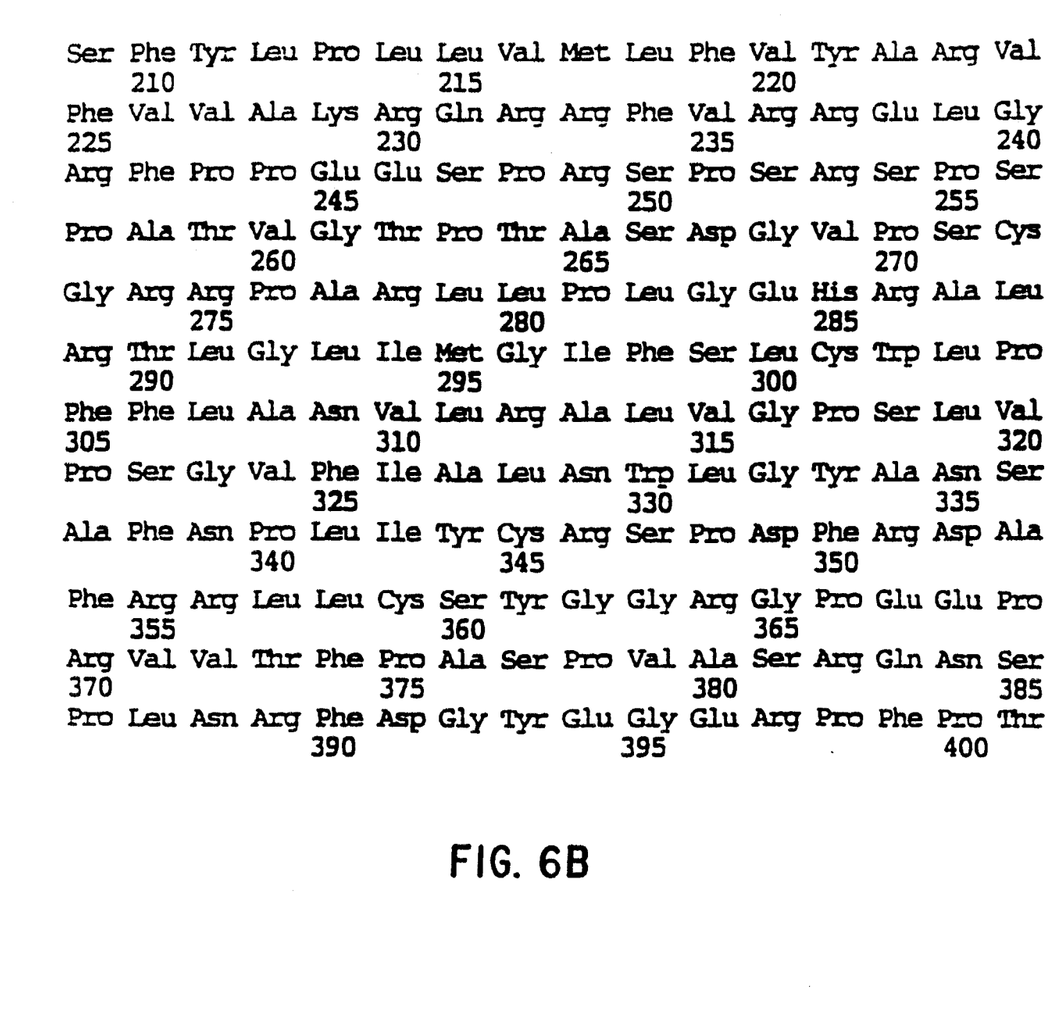

Since it is possible that the decrease in tissue responsiveness may reflect changes in β-adrenergic receptor expression, we examined the levels of β-adrenergic receptor mRNA in obese (fa/fa) Zucker rats and lean control (Fa/Fa) animals. Male obese (fa/fa) Zuker and lean (Fa/Fa) control rats (9 weeks old) was isolated and Northern blot analysis was performed. The Student's unpaired t-test was used to determine statistical significance.) . As shown in FIG. 5, β$_1$ and β$_2$-adrenergic receptor mRNA levels are unchanged in brown and white fat of obese rats. In contrast, the level of ⊖$_{3A}$-adrenergic receptor mRNA is decreased by 60% and 71%, respectively, in brown and white fat of obese animals as compared with lean controls. The selective decrease in ⊖$_{3A}$-adrenergic receptor could account for the observed catecholamine resistance of obese animals (P. Muzzin et al, Biochem. J. 261, 721 (1989)).

Accordingly, the ⊖$_{3A}$-adrenergic receptor according to the present invention, which is expressed in adipose tissue differs significantly from β$_1$-, β$_2$-, and β$_3$-adrenergic receptors previously described (C. A. Machida et al., J. Biol. hem. 265, 12960 (1990); F. Z. Chung et al., FEBS Lett. 211, 200 (1987)). Identification of this unique β-adrenergic receptor in adipose tissue of rats and humans and the demonstration that receptor mRNA levels are markedly reduced in an animal model of genetic obesity provide a basis for detection and regulation of this receptor in physiological and pathological conditions in rodents and man.

As is clear from the above experimental data and comparisons between the present receptor polypeptide and that of the prior art, the present $\ominus_{3,4}$-adrenergic receptor and its applications are a significant advancement over the prior art. The advancements are very useful to treat or study obesity.

The foregoing description of the specific embodiments will so fully reveal the general nature of the invention that others can by applying current knowledge, readily modify and/or adapt for various applications such specific embodiments without departing from the generic concept and therefore such adaptations are intended to be comprehended within the meaning and range of equivalents of the disclosed embodiments. It is to be understood that the phraseology or terminology employed herein is for the purpose of description only and not of limitation.

We claim:

1. A stably transfected, cloned Chinese Hamster Ovary cell line which expresses a rat $\beta_{3A}$-adrenergic receptor polypeptide having the amino acid sequence according to SEQ ID NO:1, wherein said polypeptide positively mediates lipolysis in rats, and wherein binding of $^{125}$I-ICYP to said $\beta_{3A}$ receptor is inhibited, in order of decreasing relative inhibition, by the agonists BRL37344, (−) isoproterenol, epinephrine, norepinephrine, and (+) isoproterenol, said cell line being deposited as American Type Culture Collection Accession No. CRL 11628.

* * * * *